United States Patent
Morriss et al.

(10) Patent No.: US 9,681,988 B2
(45) Date of Patent: Jun. 20, 2017

(54) SILENT EFFUSION REMOVAL

(71) Applicant: Acclarent, Inc., Menlo Park, CA (US)

(72) Inventors: John H. Morriss, San Francisco, CA (US); Greg Liu, Sunnyvale, CA (US); Rohit Girotra, Mountain View, CA (US); Tom Thanh Vo, Mountain View, CA (US); Richard Roy Newhauser, Jr., Redwood City, CA (US); Thomas R. Jenkins, Alameda, CA (US); Joshua Makower, Los Altos, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 14/722,337

(22) Filed: May 27, 2015

(65) Prior Publication Data
US 2015/0328051 A1   Nov. 19, 2015

Related U.S. Application Data

(63) Continuation of application No. 12/645,339, filed on Dec. 22, 2009, now Pat. No. 9,078,783.

(60) Provisional application No. 61/140,805, filed on Dec. 24, 2008.

(51) Int. Cl.
  *A61F 11/00* (2006.01)
  *A61M 1/00* (2006.01)
  *A61M 3/02* (2006.01)

(52) U.S. Cl.
  CPC .......... *A61F 11/002* (2013.01); *A61M 1/008* (2013.01); *A61M 1/0031* (2013.01); *A61M 3/0262* (2013.01); *A61M 3/0279* (2013.01); *A61F 11/006* (2013.01); *A61M 2210/0675* (2013.01)

(58) Field of Classification Search
  CPC ... A61F 11/002; A61M 1/008; A61M 1/0031; A61M 2210/0675; A61M 3/0262; A61M 3/0279
  See application file for complete search history.

(56) References Cited

U.S. PATENT DOCUMENTS

| 858,673 A | 7/1907 | Roswell |
| 1,920,006 A | 7/1933 | Deozier |
| 3,741,197 A | 6/1973 | Sanz et al. |

(Continued)

FOREIGN PATENT DOCUMENTS

| CH | 160 583 A | 3/1933 |
| CN | 86105171 | 3/1987 |

(Continued)

OTHER PUBLICATIONS

Comeau, M. et al 'Local Anesthesia of the Ear by Iontophoresis' (1973) Arch Otolaryngology. vol. 98 pp. 114-120 Abstract only.

(Continued)

*Primary Examiner* — Julie A Szpira
(74) *Attorney, Agent, or Firm* — Frost Brown Todd LLC

(57) ABSTRACT

A method is disclosed for clearing effusion from an ear. The method may include applying liquid to an ear canal, which is proximal to a perforated tympanic membrane, which is proximal to a middle ear containing effusion, applying an ear device to seal and pressurize the liquid inside the ear canal, the ear device regulating the amount of pressure inside the ear canal, and inducing a Eustachian tube, which is distal to the middle ear, to open, which causes the fluid to displace the effusion into the Eustachian tube.

20 Claims, 14 Drawing Sheets

(56) References Cited

U.S. PATENT DOCUMENTS

| | | | |
|---|---|---|---|
| 3,897,786 A | 8/1975 | Garnett et al. | |
| 3,913,584 A | 10/1975 | Walchle et al. | |
| 3,948,271 A | 4/1976 | Akiyama | |
| 3,991,755 A | 11/1976 | Vernon et al. | |
| 4,468,218 A | 8/1984 | Armstrong | |
| 4,473,073 A | 9/1984 | Darnell | |
| 4,564,009 A | 1/1986 | Brinkhoff | |
| 4,641,663 A | 2/1987 | Juhn | |
| 4,712,537 A | 12/1987 | Pender | |
| 4,971,076 A | 11/1990 | Densert et al. | |
| 5,024,612 A | 6/1991 | Van Den Honert et al. | |
| 5,026,378 A | 6/1991 | Goldsmith, III | |
| 5,044,373 A | 9/1991 | Northeved et al. | |
| 5,053,040 A | 10/1991 | Goldsmith, III | |
| 5,107,861 A * | 4/1992 | Narboni | A61F 13/38 128/846 |
| 5,129,402 A * | 7/1992 | Koll | A61B 10/04 600/572 |
| 5,254,120 A | 10/1993 | Cinberg et al. | |
| 5,261,903 A | 11/1993 | Dhsliwal et al. | |
| D352,780 S | 11/1994 | Gleaser et al. | |
| 5,421,818 A | 6/1995 | Arenberg et al. | |
| 5,466,239 A | 11/1995 | Cinberg et al. | |
| 5,496,329 A | 3/1996 | Reisinger | |
| 5,554,071 A | 9/1996 | Peltola et al. | |
| D378,611 S | 3/1997 | Croley | |
| 5,610,988 A | 3/1997 | Miyahara | |
| 5,643,280 A | 7/1997 | Del Rio et al. | |
| 5,665,094 A * | 9/1997 | Goldenberg | A61F 11/004 604/212 |
| 5,674,196 A | 10/1997 | Donaldson et al. | |
| D387,863 S | 12/1997 | Herman et al. | |
| 5,707,383 A * | 1/1998 | Bays | A61F 11/004 128/898 |
| 5,792,100 A | 8/1998 | Shantha | |
| 5,827,295 A | 10/1998 | Del Rio et al. | |
| 5,893,828 A | 4/1999 | Uram | |
| 5,944,711 A | 8/1999 | Pender | |
| D418,223 S | 12/1999 | Phipps et al. | |
| D420,741 S | 2/2000 | Croley | |
| 6,045,528 A | 4/2000 | Arenberg et al. | |
| D424,197 S | 5/2000 | Sydlowski et al. | |
| 6,059,803 A * | 5/2000 | Spilman | A61M 1/0023 604/319 |
| D426,135 S | 6/2000 | Lee | |
| 6,137,889 A | 10/2000 | Shennib et al. | |
| 6,183,469 B1 | 2/2001 | Thapliyal et al. | |
| 6,200,280 B1 | 3/2001 | Brenneman et al. | |
| 6,245,077 B1 | 6/2001 | East et al. | |
| 6,251,121 B1 | 6/2001 | Saadat | |
| D450,843 S | 11/2001 | McGuckin, Jr. et al. | |
| 6,358,231 B1 | 3/2002 | Schindler et al. | |
| 6,440,102 B1 * | 8/2002 | Arenberg | A61F 11/00 604/506 |
| 6,475,138 B1 | 11/2002 | Schechter et al. | |
| 6,520,939 B2 | 2/2003 | Lafontaine | |
| 6,522,827 B1 | 2/2003 | Loeb et al. | |
| 6,645,173 B1 | 11/2003 | Liebowitz | |
| 6,648,873 B2 | 11/2003 | Arenberg et al. | |
| 6,663,575 B2 | 12/2003 | Leysieffer | |
| 6,682,558 B2 | 1/2004 | Tu et al. | |
| 6,770,080 B2 | 8/2004 | Kaplan et al. | |
| 6,790,171 B1 | 9/2004 | Grundeman et al. | |
| 6,916,159 B2 | 7/2005 | Rush et al. | |
| 7,127,285 B2 | 10/2006 | Henley et al. | |
| D535,027 S | 1/2007 | James et al. | |
| 7,160,274 B2 | 1/2007 | Ciok et al. | |
| 7,344,507 B2 | 3/2008 | Briggs et al. | |
| 7,351,246 B2 | 4/2008 | Epley | |
| 7,381,210 B2 | 6/2008 | Zarbatany et al. | |
| D595,410 S | 6/2009 | Luzon | |
| 7,563,239 B1 | 7/2009 | Hudson et al. | |
| D598,543 S | 8/2009 | Vogel et al. | |
| 7,654,997 B2 | 2/2010 | Makower et al. | |
| 7,677,734 B2 | 3/2010 | Wallace | |
| 7,704,259 B2 | 4/2010 | Kaplan et al. | |
| 7,749,254 B2 | 7/2010 | Sobelman et al. | |
| D622,842 S | 8/2010 | Benoist | |
| 8,192,420 B2 | 6/2012 | Morriss et al. | |
| 8,409,175 B2 | 4/2013 | Lee et al. | |
| 8,425,488 B2 | 4/2013 | Clifford et al. | |
| 8,498,425 B2 | 7/2013 | Graylin | |
| 8,518,098 B2 | 8/2013 | Roeder et al. | |
| 9,078,783 B2 | 7/2015 | Morriss et al. | |
| 2002/0069883 A1 | 6/2002 | Hirchenbain | |
| 2002/0138091 A1 * | 9/2002 | Pflueger | A61B 10/0266 606/170 |
| 2005/0182385 A1 * | 8/2005 | Epley | A61F 11/00 604/514 |
| 2007/0100300 A1 | 5/2007 | Hashemian | |
| 2008/0051804 A1 | 2/2008 | Cottler et al. | |
| 2008/0212416 A1 | 9/2008 | Polonio et al. | |
| 2008/0262510 A1 | 10/2008 | Clifford | |
| 2008/0300527 A1 | 12/2008 | Bivins | |
| 2010/0061581 A1 | 3/2010 | Soetejo et al. | |
| 2010/0274188 A1 * | 10/2010 | Chang | A61B 1/227 604/96.01 |

FOREIGN PATENT DOCUMENTS

| | | |
|---|---|---|
| DE | 19618585 | 11/1997 |
| EP | 0214527 | 1/1991 |
| EP | 1 034 808 A1 | 9/2000 |
| FR | 2526656 | 11/1983 |
| RU | 2091672 | 9/1997 |
| WO | WO 2006/059961 | 6/2006 |
| WO | WO 2006/119512 | 11/2006 |
| WO | WO 2008/030485 | 3/2008 |
| WO | WO 2008/036368 | 3/2008 |
| WO | WO 2009/010788 | 1/2009 |

OTHER PUBLICATIONS

Comeau, M. et al 'Local Anesthesia of the Human Tympanic Membrane by the Iontophoresis of a Local Anesthetic Nov. 9, 1978' The Laryngoscope vol. 88 pp. 277-285.

Echols, D.F. et al 'Local Anesthesia of the Ear by Iontophoresis of Lidocaine' (1973) Arch Otolaryngology. vol. 101 pp. 418-421 Abstract only.

Epley, J.M. 'Modified technique of Iontophoretic Anesthesia for Myringotomy in Children' (1977) Arch Otolaryngology. vol. 103 pp. 358-360.

Hasegawa, M. et al. 'Iontophorectic Anesthesia of the Tympanic Membrane' (1978) Clinical Otolaryngology. vol. 3 pp. 63-66 Abstract only.

Medtronic XOMED, Activent® Antimicrobial Ventilation Tubes Advertisement, 2002, 4 pages.

Micromedics Innovative Surgical Products [retrieved on Jul. 15, 2010] Retrieved from the Internet <URL: http://www.micromedics-usa.com/products/otology/micromedicstubes.htm. 7 pages.

Plenum' Compact Oxford English Dictionary <http://oxford-dictionaries.com/definition/english/plenum>.

Plenum' Merriam-Webster's Online Dictionary <http://merriam-webster.com/definition/english/plenum>.

Ramsden, R.T. et al. 'Anesthesia of the Tympanic Membrane Using Iontophoresis' (1977) The Journal of Laryngology and Otology. vol. 56, No. 9. pp. 779-785.

Australian Patent Examination Report No. 1 dated Jan. 2, 2015 re Application No. 2009329902.

Australian Patent Examination Report No. 2 dated Aug. 25, 2015 re Application No. 2009329902.

Chinese First Office Action dated Feb. 17, 2013 for Application No. CN 200980153120.2, 6 pages.

Chinese Search Report dated Jan. 16, 2013 for Application No. CN 200980153120.2, 2 pages.

International Preliminary Report on Patentability dated Nov. 17, 2009 re Application No. PCT/US2008/060779.

(56) References Cited

OTHER PUBLICATIONS

International Preliminary Report on Patentability dated Jun. 29, 2011 for Application No. PCT/US2009/069388, 10 pages.
International Search Report (and Written Opinion) dated Nov. 6, 2009 re Application No. PCT/US2009/052395.
International Search Report (and Written Opinion) dated Jun. 30, 2010 re Application No. PCT/US2009/069388.
International Search Report (and Written Opinion) dated Aug. 27, 2010 re Application No. PCT/US2010/042128.
International Search Report (and Written Opinion) dated Feb. 17, 2011 re Application No. PCT/US2010/058718.
Japanese Office Action, Notification of Reasons for Refusal, dated Oct. 15, 2013 for Application No. JP 2011-543674, 3 pages.
Japanese Office Action, Notification of Reasons for Refusal, dated Mar. 18, 2014 for Application No. JP 2011-543674, 3 pages.
Mexican Examiner's Report dated Mar. 18, 2014 for Application No. MX/a/2011/006854, 2 pages.
Mexican Examiner's Report dated Sep. 29, 2014 for Application No. MX/a/2011/006854, 2 pages.
Mexican Examiner's Report dated Jan. 23, 2015 for Application No. MX/a/2011/006854, 2 pages.
Russian Office Action dated Apr. 2, 2014 for Application No. RU 2011130914/14, 17 pages.
U.S. Appl. No. 61/085,360, filed Jul. 31, 2008.
U.S. Appl. No. 61/140,805, filed Dec. 24, 2008.
European Search Report and Written Opinion dated Oct. 12, 2016 for Application No. EP 16176477.4, 13 pgs.
Partial European Search Report dated Sep. 5, 2016 for Application No. EP 16176477.4, 7 pgs.
International Search Report dated Sep. 3, 2008 for Application No. PCT/US2008/60779, 1 pg.

\* cited by examiner

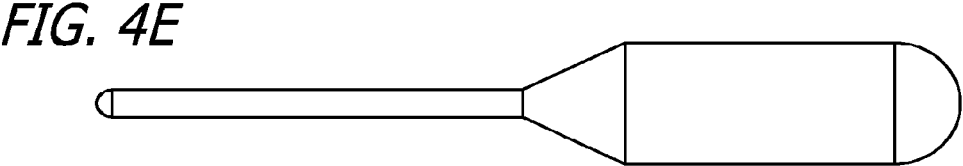
FIG. 4E
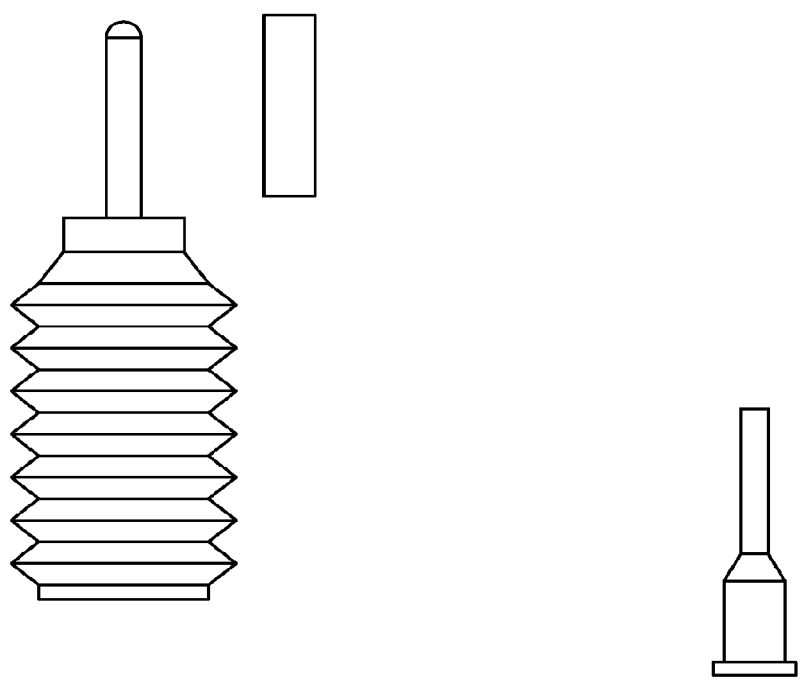
FIG. 4F
FIG. 4G
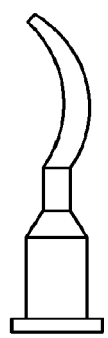
FIG. 4H
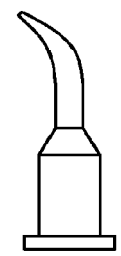
FIG. 4I

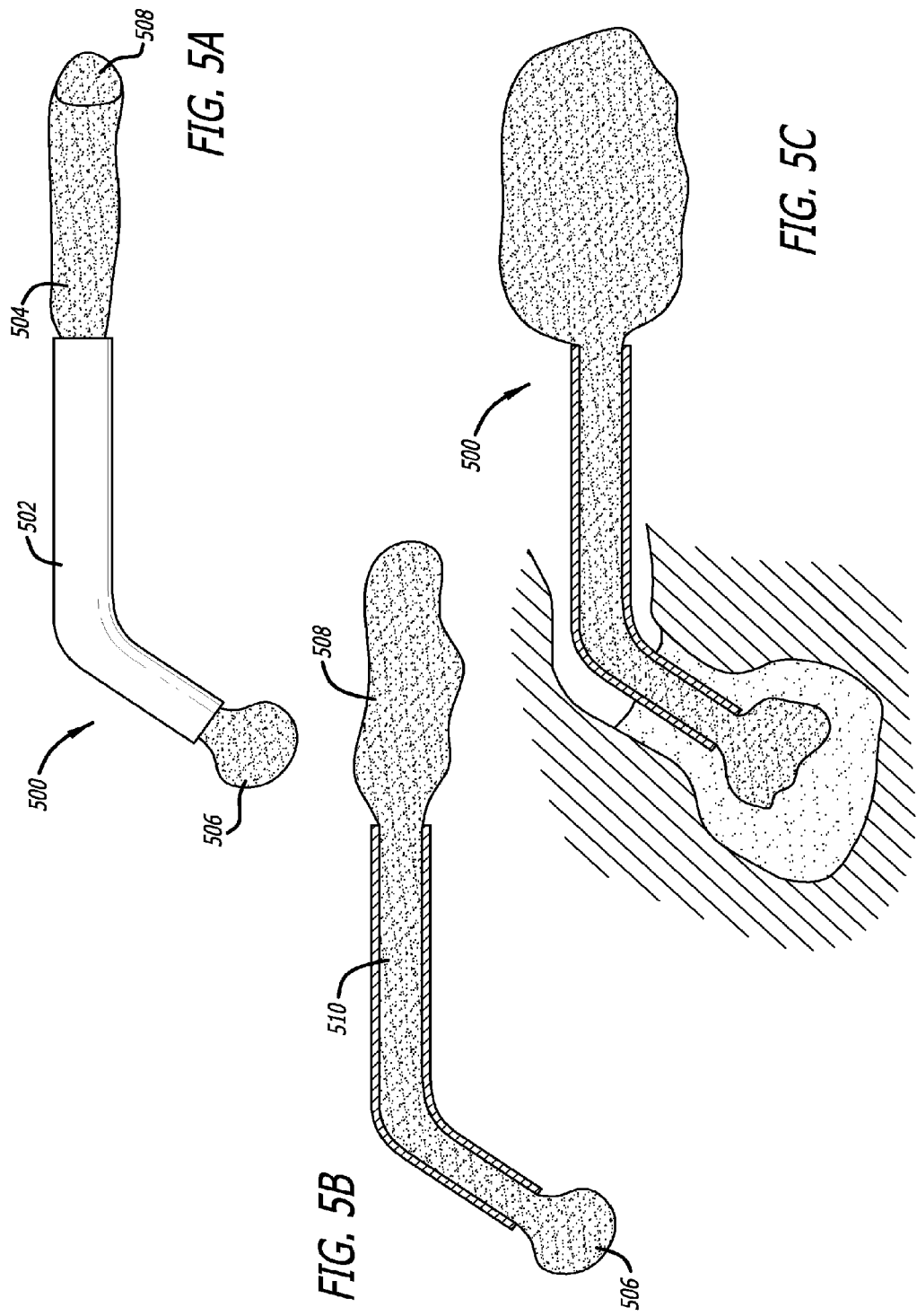

SILENT EFFUSION REMOVAL

This application is a continuation of U.S. patent application Ser. No. 12/645,339, entitled "Silent Effusion Removal," filed Dec. 22, 2009 (now U.S. Pat. No. 9,078,783), which claims the benefit of U.S. Provisional Application No. 61/140,805, also entitled "Silent Effusion Removal," filed Dec. 24, 2008, the entirety of which is incorporated by reference herein for all purposes.

FIELD OF THE INVENTION

The invention generally relates to methods and devices for treatment of the ear, which may be supplemental to a tympanocentesis procedure.

BACKGROUND OF THE INVENTION

Middle ear infections are common in young children. Suffering may be alleviated by puncturing the tympanic membrane to evacuate the fluid, a treatment known as tympanocentesis. The patient may undergo general anesthesia prior to a tympanocentesis procedure, but this is not preferred due to cost and health concerns. As a preferable alternative, the tympanic membrane can be locally anesthetized with an iontophoresis procedure. Thus, the patient may be treated while awake. Devices and methods for locally anesthetizing the tympanic membrane are disclosed in co-assigned patent applications U.S. Ser. No. 11/962,063 (now U.S. Pat. No. 8,192,420), U.S. Ser. No. 11/749,729 (published as U.S. Pub. No. 2008/0262510), now U.S. Pat. No. 9,387,124, issued Jul. 12, 2016), and U.S. 61/085,360, the entireties of which are incorporated by reference herein. Figure 1A shows a view of an outer ear. The outer ear includes a major element known as the Auricle or Pinna 100. The outer ear serves as a funnel for directing sounds into the internal portions of the ear. The major physical features of the ear include the Lobule 102, Concha 104, Athelix 106, Helix 108, Scapha 110, Triangular fossa 112, Externam acoustic meatus 114, Tragus 116, and Antitragus 118.

FIG. 1B shows a cross-section of the inner and outer portions of the ear. The pinna 100 is shown connected to the External auditory meatus 118, or ear canal. The ear canal 118 is shown as a relatively straight passage, but is often a tortuous passageway. The ear canal 118 is connected to the middle ear 120, which includes the ear drum 122. The middle ear 120 in turn is connected to the internal ear 124. When the middle ear 120 becomes infected, fluid swells inside the ear drum 122. Fluid expansion causes extreme pain to one with a middle ear infection.

Fluid in the middle ear is commonly known as serous otitis media or "effusion". Effusion is normally drained through the tympanocentesis procedure. However, effusion may thicken and thus be difficult to remove or drain. Thickening of effusion is common with patients who suffer from chronic ear infections. Accordingly, a tympanocentesis procedure may not be effective in patients with lodged or thickened effusion.

Tympanocentesis procedures, which implement iontophoresis, often require iontophoresis fluid to be evacuated before the tympanic membrane is punctured. Evacuation of fluid is commonly performed through low pressure suction via a syringe or suction cannula. Fluid evacuation is often a painful and uncomfortable process because large amounts of noise are created by fluid cavitation. Thus, fluid evacuation by suction may cause pain and emotional discomfort which may prevent the completion of the tympanocentesis procedure. It should be noted that many patients are young, 5 and under, and also have endured many hours or days of a painful ear infection, and thus may be uncooperative and difficult to treat. Fluid may also be removed by swabbing the ear with an absorbent material, however this can be irritating to the patient and ineffective as well. Swabbing also requires the patient to vigorously shake their head side to side, which many young patients refuse to comply with.

BRIEF SUMMARY OF THE INVENTION

One embodiment of the invention may include a method for clearing effusion from an ear. The method may include applying liquid to an ear canal, which is proximal to a perforated tympanic membrane, which is proximal to a middle ear containing effusion. The perforated tympanic membrane may have been intentionally perforated in a prior tympanocentesis procedure. The effusion may not have been removed by the normal tympanocentesis procedure. The method may also include applying an ear device to seal and pressurize the liquid inside the ear canal, the ear device regulating the amount of pressure inside the ear canal. The method may also include inducing a Eustachian tube, which is distal to the middle ear, to open, which causes the fluid to displace the effusion into the Eustachian tube.

Another aspect of the invention may include a method for clearing effusion from an ear, the method including applying an ear device to seal an ear canal, which is proximal to a perforated tympanic membrane, which is proximal to a middle ear containing effusion. The method may also include pressurizing the ear canal with air, and inducing a Eustachian tube, which is distal to the middle ear, to open, which causes the pressurized air to displace the effusion into the Eustachian tube.

Yet another aspect of the invention may include a device for pressurizing an ear canal, the device including a first ear cup which encloses a first external ear, the first ear cup having a first sealing member which fluidly seals around the first external ear, the first ear cup having a first port which is in fluid communication with the sealed first external ear. The device may also include a second ear cup which encloses a second external ear, the second ear cup having a second sealing member which fluidly seals around the second external ear, the second ear cup having a second port which is in fluid communication with the sealed second external ear. A headpiece may connect to each ear cup, the headpiece being configured for applying sealing pressure to each sealing member and retaining each ear cup on each respective external ear.

Yet another aspect of the invention may include a method for clearing liquid from an ear canal, the method including applying a device including a wicking tip to a liquid solution inside an ear canal to wick the liquid from the ear canal. The liquid may be left from a iontophoresis procedure. The method may also include applying negative pressure to the device to aid in wicking the liquid, wherein the wicking tip regulates turbulence to reduce noise caused by wicking the liquid.

Yet another aspect of the invention may include a device for clearing liquid from an ear canal, the device including an elongated cannula including a first end and a second end. The device may also include an elongated foam member including a distal end and a proximal end, a portion of the elongated foam member compressed within the cannula, the distal end uncompressed and exposed past the first end, the proximal end uncompressed and exposed past the second end, wherein the proximal end is larger than the distal end to provide a wicking action to the distal end, and wherein the proximal end will enlarge when fluid is wicked from the distal end into the proximal end.

Yet another aspect of the invention may include a device for silently removing liquid from an ear canal, the device including an elongated multi-lumen cannula including a distal end and a proximal end, wherein each lumen includes a cross-sectional area which reduces cavitation during suction. A suction apparatus may be coupled to the proximal end of the multi-lumen cannula.

Yet another aspect of the invention may include a method for removing liquid from an ear canal, the method including receiving a trigger to apply suction to a device in an ear canal filled with liquid, the device including a lumen for removing the liquid. Suction may be applied to the device. The method may also include monitoring an electrical signal from the device. The method may also include detecting an imminent creation of noise, or noise, caused by the suction; and reducing suction until the imminence of noise, or noise, subsides.

Yet another aspect of the invention may include a system for removing liquid from an ear canal. The system may include a suction probe, which includes at least one noise sensor. A pressure regulator may be coupled to the suction probe, the pressure regulator being configured to supply negative pressure to the suction probe. A processor may be electrically coupled to the at least one noise sensor and pressure regulator, the processor being configured to detect, based on signals from the at least one noise sensor, imminent creation of noise, or noise, caused by the suction probe, the processor being further configured to modify pressure supplied by the pressure regulator based on the signals.

Yet another aspect of the invention may include a device for silently removing liquid from an ear canal. The device may include an elongated cannula. Filtering material may be disposed within the cannula. A portion of the filtering material may be extended out of an end of the elongated cannula.

Yet another aspect of the invention may include a method for silently removing effusion from a middle ear. A tympanostomy tube including a central lumen may be implanted into a tympanic membrane. A device having an Archmides' screw may be inserted into the central lumen. The Archmides' screw may be actuated to remove effusion lodged adjacent to the tympanic membrane.

Yet another aspect of the invention may include a system for silently removing effusion from a middle ear. The system may include a tympanostomy tube including a central lumen. An elongated cannula may be configured to be slidably engaged with the lumen. An Archmides' screw may be rotatably disposed within the cannula.

To better understand the nature and advantages of the invention, reference should be made to the following description and the accompanying figures. It is to be understood, however, that the figures and descriptions of exemplary embodiments are provided for the purpose of illustration only and are not intended as a definition of the limits of the scope of the present invention.

BRIEF DESCRIPTION OF THE DRAWINGS

FIGS. 4A-4F show frontal views of liquid removal devices, according to embodiments of the invention.
FIGS. 4G-4I shows frontal views of liquid removal nozzles, according to embodiments of the invention.
FIG. 5A shows a side view of a device for silently removing liquid from an ear, according to one embodiment of the invention.
FIG. 5B shows a cross-sectional view of a device for silently removing liquid from an ear, according to one embodiment of the invention.
FIG. 5C shows a cross-sectional view of a device for silently removing liquid from an ear in use, according to one embodiment of the invention.

DETAILED DESCRIPTION OF THE INVENTION

Figure 1A:
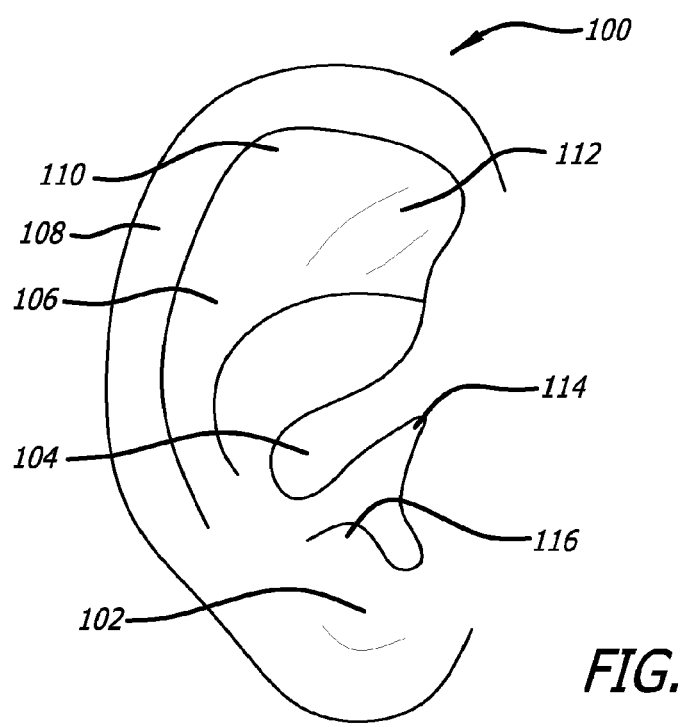
FIG. 1A shows a direct view of an outer ear.
Figure 1B:
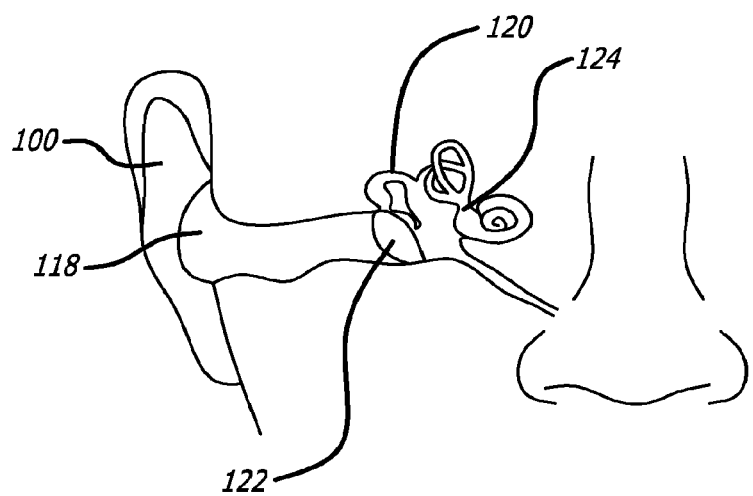
FIG. 1B shows a cross-sectional view of an outer, middle, and inner ear, and a Eustachian tube.
Figure 2A:
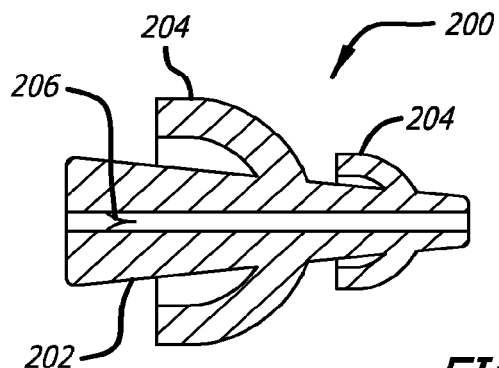
FIG. 2A shows a cross-sectional view of an earplug, according to one embodiment of the invention.

Effusion Removal:

FIG. 2A shows an earplug 200, according to one embodiment of the invention. The earplug 200 includes a main lumen 202. One or more sealing members 204 extend from the main lumen 202. The sealing members 204 are umbrella shaped, and configured to partially deform within an ear canal to form a fluid tight seal. The sealing members 204 are shown to be integral from the main lumen 202, but may also be separately attached. The sealing members 204 are preferentially more flexible than the main lumen 202, as the main lumen 202 should remain at least partially open in use. A lumen seal 206 is placed within the main lumen 202, which prevents fluid and pressure from exiting the lumen. The lumen seal 206 is shown configured as a duckbill valve, but may include other configurations. For example, the lumen seal 206 may be an elastomeric plug, or wall, with a compressed lumen, which may be expanded by a device for inserting fluid, such as a syringe. The earplug 200 may be constructed from various flexible materials, for example rubber or silicone. Various configurations of the earplug 200 are possible, such as shown in previously incorporated by reference U.S. Provisional Patent Application No. U.S. 61/085,360.

Figure 2B:
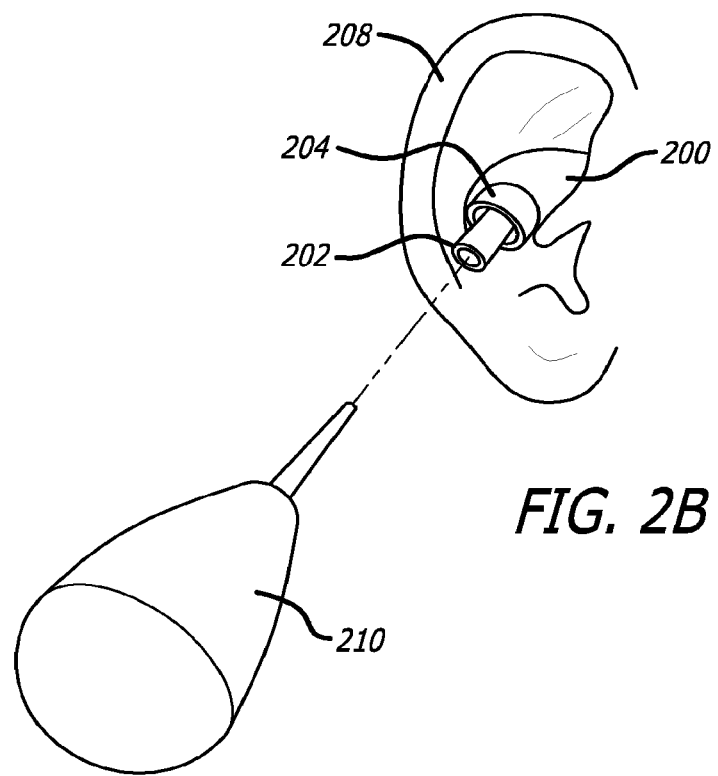
FIG. 2B shows a perspective view of an earplug in use, according to one embodiment of the invention.

FIG. 2B shows the earplug 200 in use, according to one embodiment of the invention. As shown, a portion of the earplug 200 has been inserted into an ear canal and another portion remains exposed adjacent to the outer ear 208. The ear shown may have undergone a tympanocentesis procedure, shortly before insertion of the earplug. A sealing member 204 is also shown in a partially compressed state. Thus, the earplug 200 is fluidly sealed within the ear canal. A bulb device 210 or syringe may be coupled with the earplug to supply fluidic pressure into the ear canal. The fluid may be a liquid, such as iontophoresis fluid, saline, or water, or a gas, such as air. As the ear has undergone a tympanocentesis procedure, the tympanic membrane has been punctured, and the ear canal 118 is in fluidic communication with the middle ear 120. The patient may be instructed to swallow, and thus induce the Eustachian tube to open. This action causes a pressure differential between the Eustachian tube and the ear canal. Thus, fluid in the ear canal will pass through the middle ear, and flush solid or semi-solid effusion inside the middle ear into the Eustachian tube. Alternatively, the bulb device 210 may be used without instructing the patient to swallow. Creating a large enough pressure differential between the ear canal and Eustachian tube will force the Eustachian tube to open and move fluid through the middle ear. Care should be taken to avoid damage to the tympanic membrane. In an alternative embodiment, a relief valve is included to prevent over-pressurization of the ear canal. This procedure may also be performed on both ears simultaneously, and with the patient sitting upright.

Figure 2C:
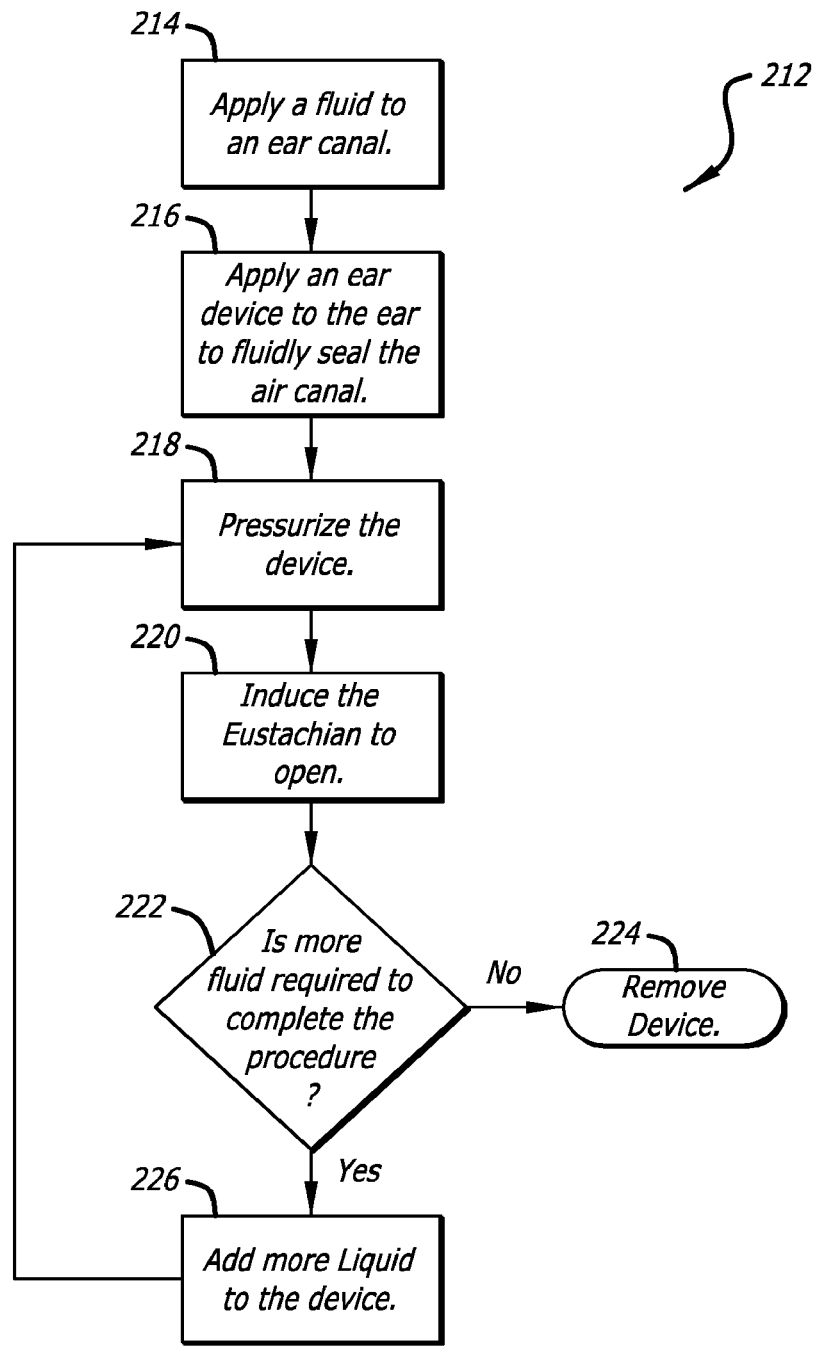
FIG. 2C shows a flow chart of a method for removing effusion from a middle ear, according to one embodiment of the invention.

FIG. 2C shows a flow chart of a method 212 for removing effusion from a middle ear, according to one embodiment of the invention. In operation 214, a liquid is applied to the ear canal. The fluid may be liquid such as iontophoresis fluid, saline, or water. The liquid is preferably at room temperature, or higher, in order to prevent discomfort to the patient. In an alternative embodiment, no liquid is provided for operation 214, and the method begins at operation 216 using only gas as a fluid. At operation 216 an ear device is applied to the ear canal of the patient, to form a fluid tight seal between the ear canal and the surrounding atmosphere. The ear device may, for example, be device 200 as shown in FIGS. 2A and 2B. At operation 218 the ear device is pressurized with fluid, which may be a gas or liquid. The ear device may be pressurized with an external device such as a syringe, catheter, or bulb device as shown in FIG. 2B. At operation 220 the Eustachian tube is induced to open, which may occur from the patient swallowing or from the pressure created in operation 218. In operation 222 it is determined whether more fluid is required to complete the procedure. If not, then the procedure is complete and ends at 224. If more fluid is required then the method 212 reverts to operation 218.

Figure 2D:
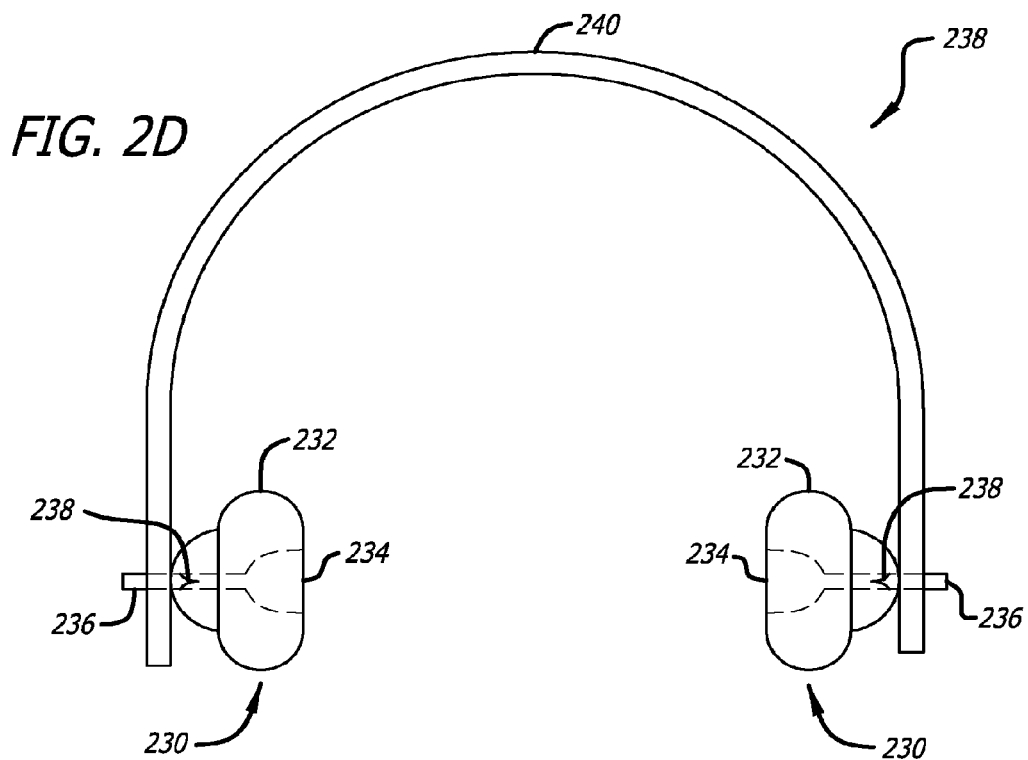
FIG. 2D shows a frontal view of a device for sealing both ears of a patient, according to one embodiment of the invention.
Figure 2E:
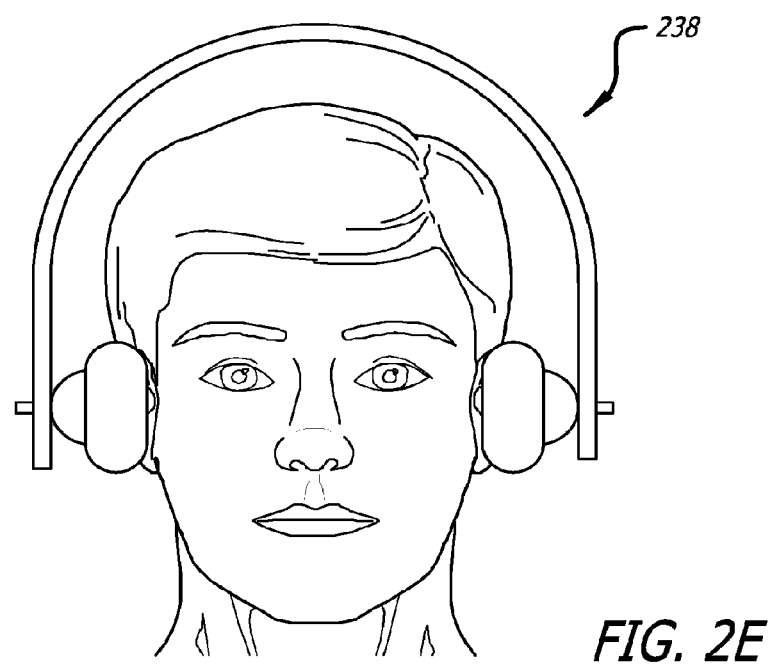
FIG. 2E shows a frontal view of a device for sealing both ears of a patient in use, according to one embodiment of the invention.

FIG. 2D shows a device 228 for sealing both ears of a patient, according to one embodiment of the invention. The device includes ear cups 230. Each ear cup 230 includes sealing members 232, which are configured to fit over and fluidly seal the outer ear of a patient. Each ear cup 230 is provided with a fluid chamber 234, which fluidly communicates with an ear canal. Each fluid chamber 234 in turn is in fluid communication with a port 236. The ports 236 include seals 238 for sealing the fluid chambers from the external atmosphere. The seals 238 may be constructed from a flexible material, such as silicone or rubber. The ports 236 may couple to an external device which provides fluidic pressure, for example a syringe, catheter, or bulb device as shown in FIG. 2B. In an alternative embodiment each port 236 is connected to an integral air pump, which pressurizes each fluid chamber when manually or electrically activated. In another alternative embodiment, a relief valve is included to prevent over-pressurization of the ear canal. A band 240 connects each ear cup 230, and provides spring force for sealing each ear cup 230 to a patient's head. FIG. 2E shows a front view of patient wearing the device 228.

Figure 2F:
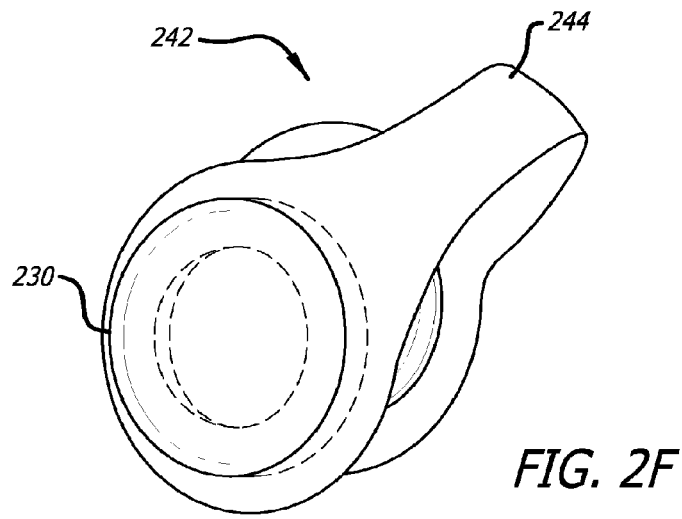
FIG. 2F shows a perspective view of a device for sealing both ears of a patient, according to one embodiment of the invention.
Figure 2G:
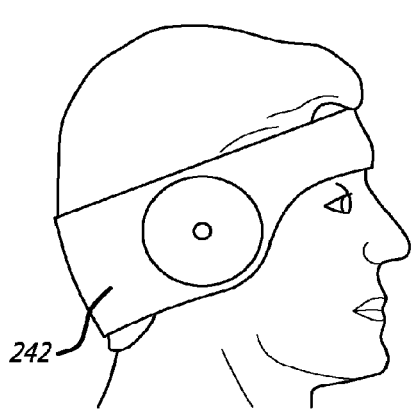
FIGS. 2G and 2H show frontal and side views, respectively, of a device for sealing both ears of a patient in use, according to one embodiment of the invention.
Figure 2H:
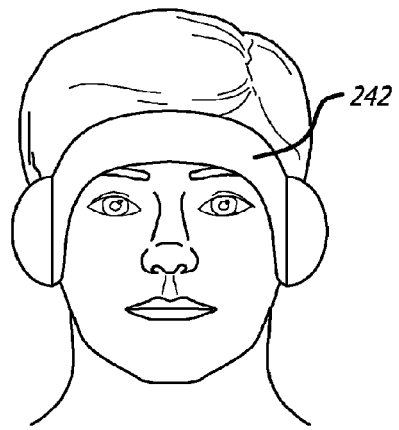

FIG. 2F shows a device 242 for sealing both ears of a patient, according to one embodiment of the invention. The device includes ear cups 230, which may be constructed as described regarding FIG. 2D. The device 242 includes a wrap-around headband 242. The headband 242 wraps around the entire head of a patient, and thus will not easily be disturbed during a procedure. The headband may be constructed from an elastic material, such as rubber or silicone. FIGS. 2G and 211 show side and front views, respectively, of the device 242 in use on a patient.

Figure 3A:
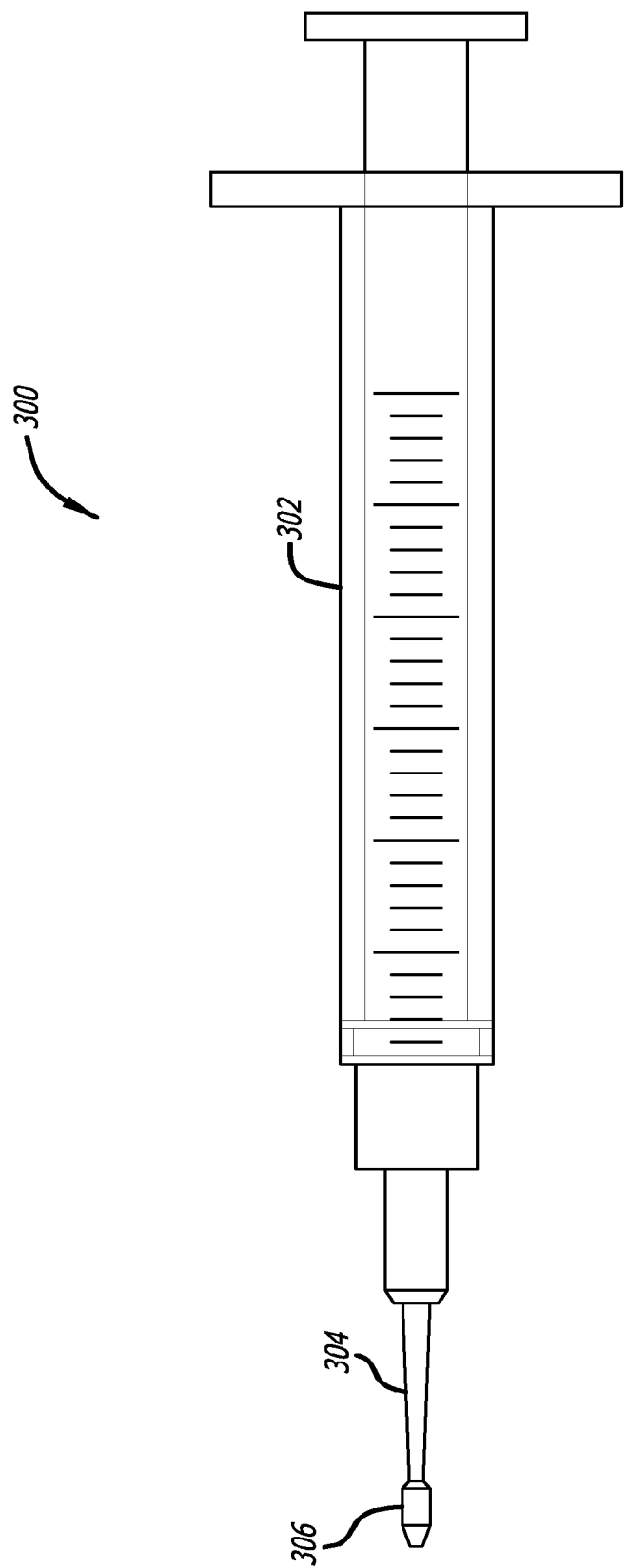
FIG. 3A shows a side view of a device for silently removing liquid from an ear, according to one embodiment of the invention.

Silent Liquid Removal:

FIG. 3A shows a device 300 for silently removing liquid from a patient's ear, according to one embodiment of the invention. Removing liquid in the ear after a tympanocentesis procedure may be very disturbing to a patient, as a large amount of noise is created in the ear by conventional suction devices. The device 300 includes a syringe 302, a nozzle 304, and an absorbent tip 306. The syringe 302 provides negative pressure for suctioning and retaining liquid. The nozzle 304 should be flexible to allow insertion into a tortuous ear canal without causing patient discomfort. The nozzle 304 should also be flexible and long enough to reach the tympanic membrane without buckling or kinking. The nozzle 304 may be constructed from a polymer, for example nylon, polycarbonate, polypropylene, polyethylene, silicone, or an annealed or super elastic alloy. The distal portion of the nozzle 304 may include an outer diameter ranging from 0.5-3.0 mm, which allows passage through a speculum and visualization past the nozzle to ensure proper placement within the ear canal. The proximal portion of the nozzle 304 includes a luer fitting for coupling to the syringe 302. The absorbent tip 306 is located within the distal portion of the nozzle 304. The absorbent tip 306 may be constructed from absorbent materials such as porous fibers or foam, which will wick liquids. Suitable materials include polyvinyl acetate, rayon, and various blends of the two materials. The absorbent tip 306 may include pore sizes and interstitial spaces which attract liquid and retain particles. The absorbent tip 306 may extend 1-5 mm past the distal portion of the nozzle.

Figure 3B:
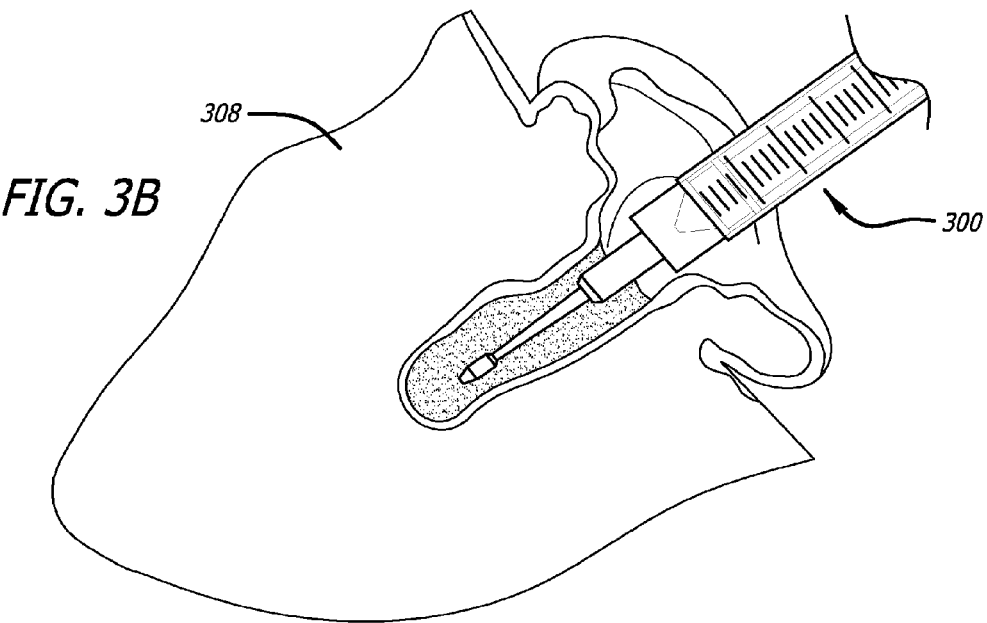
FIGS. 3B and 3C show frontal views of a device for silently removing liquid from an ear in use, according to one embodiment of the invention.
Figure 3C:
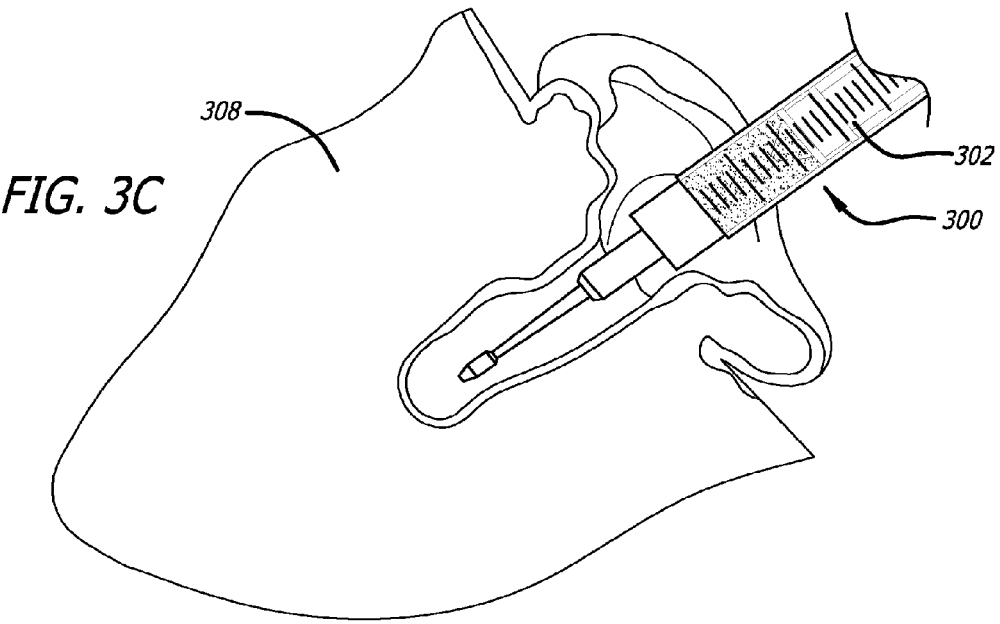

FIG. 3B shows device 300 in use, according to one embodiment of the invention. The device 300 is shown in use in an ear canal model 308 which is partially filled with a liquid solution. The absorbent tip 306 is initially placed in the ear canal and adjacent to the tympanic membrane. Contact with the liquid solution causes an immediate wicking action, which draws the liquid solution into the device 300. The wicking action is completely silent, and thus will not disturb a patient. FIG. 3C shows the syringe 302 has been slowly drawn back to suction the remaining liquid solution, accordingly, the liquid solution is silently and quickly removed. This method may be performed implementing a one-handed technique by the operator.

Figure 4A:
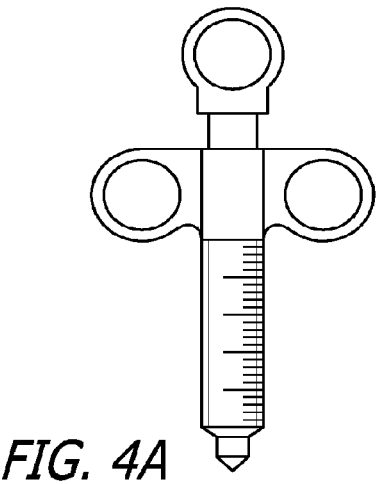
Figure 4B:
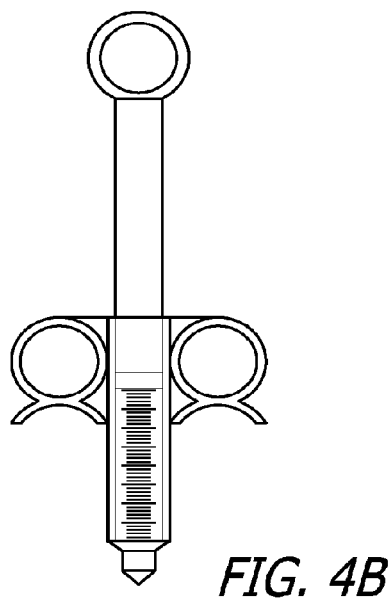
Figure 4C:
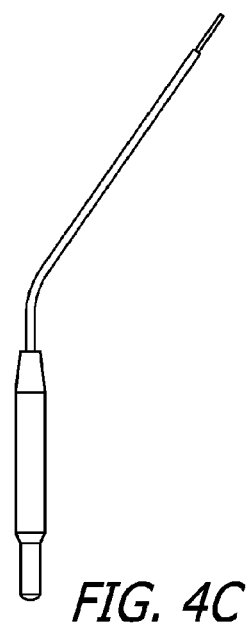
Figure 4D:
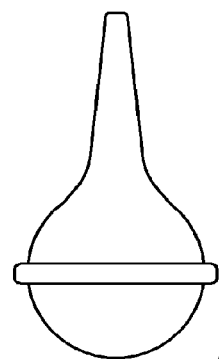

FIGS. 4A-4F show devices which may be used in lieu of the syringe 302 with respect to device 300, according to different embodiments of the invention. FIG. 4A shows a syringe with finger adapters which allows an ergonomic one-handed suction motion. FIG. 4B shows a spring-loaded syringe, which requires minimal effort to use. FIG. 4C shows a otology suction device, which may connect to a standard suction line. FIG. 4D shows a suction bulb, which is compressed before use. FIG. 4E shows a suction pipette, which is compressed before use. FIG. 4F shows a bellows-type suction device, which is compressed before use.

FIGS. 4G-4I show devices which may be used in lieu of the nozzle 304 with respect to device 300, according to different embodiments of the invention. FIG. 4G shows a straight nozzle, which may offer better visibility in use. FIGS. 4H and 4I show shapeable nozzles of different lengths, which may be shaped in the field by the operator for better access and visibility.

FIGS. 5A and 5B show a device 500 for silently removing liquid from a patient's ear, according to one embodiment of the invention. The device 500 includes an elongated cannula 502. The elongated cannula 502 may be pre-shaped to include a bend as shown, or in a straight configuration. The elongated cannula 502 may constructed from a malleable metal, and bent in the field by an operator for better access and visibility. The elongated cannula 502 includes an outer diameter which is small enough to reach the tympanic membrane, for example 1-3 mm. An elongated foam member 504 resides within the elongated cannula 502. The elongated foam member 504 includes a distal foam portion 506 and a proximal foam portion 508. The distal foam portion 506 extends past the elongated cannula 502 by a small amount, e.g. 1-3 mm, in comparison to the proximal foam portion 508. A compressed region of foam 510 resides within the elongated cannula, and connects the distal and proximal foam portions. The foam may include pore sizes which can capture particulates.

FIG. 5C shows the device 500 in use, according to one embodiment of the invention. The distal foam portion 506 is shown placed in a liquid solution. The distal foam portion 506 expands slightly upon immersion, but is largely restrained by the elongated cannula. Liquid is wicked silently from the distal foam portion 506 to the proximal foam portion 508. The proximal foam portion 508 has a larger volume than the distal foam portion 506, and thus acts as a fluid depository. Accordingly, liquid is wicked from the distal foam portion 506 to the proximal foam portion 508 in a quick and silent manner. The device 500 requires no actuation other than placement in the ear. The proximal foam portion 508 may be compressed to remove wicked fluid and reused during the procedure or in the other ear.

Figure 6A:
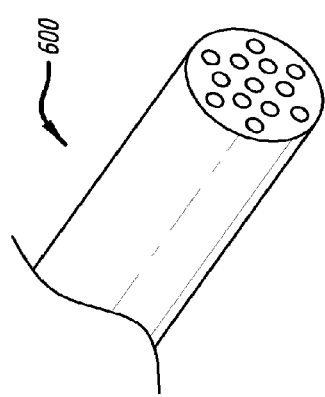
FIG. 6A shows a perspective view of a device for silently removing liquid from an ear, according to one embodiment of the invention.
Figure 6B:
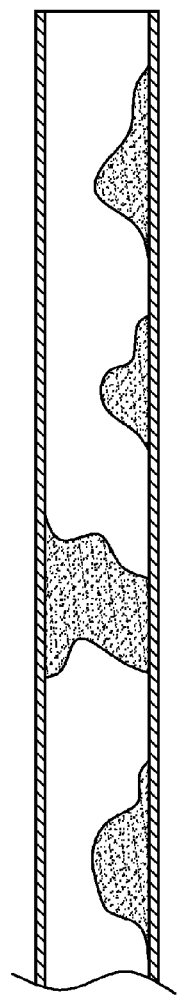
FIG. 6B shows a cross-sectional view of a prior art device for removing liquid from an ear in use.
Figure 6C:
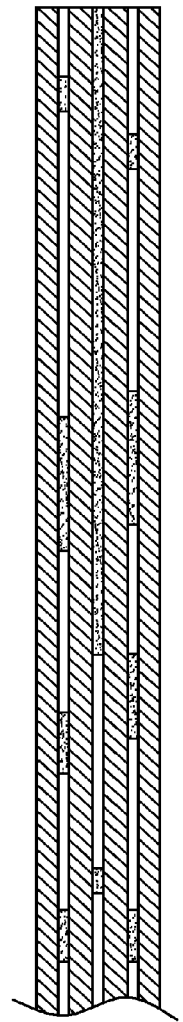
FIG. 6C shows a cross-sectional view of a device for removing liquid from an ear in use, according to one embodiment of the invention.

FIG. 6A shows a device 600 for silently removing liquid from a patient's ear, according to one embodiment of the invention. The device 600 is configured as a multi-lumen tube. The tube includes an outer diameter which is small enough to reach the tympanic membrane, for example 1-3 mm. The lumen diameters may range from 0.05-0.5 mm. The device 600 may be connected to a suction device, for example a suction line or syringe. The device may also be flexible or constructed from a malleable material. Noise may be created when air mixes with liquid in a low pressure environment to cause cavitation and create a noisy "slurping" sound, as depicted in prior art device of FIG. 6B. Thus, the larger the inner diameter of the suction device, the more likely noise will be produced, as any given cross-section of a large lumen may occupy both air and water. Device 600 prevents unwanted cavitation by using several smaller diameter lumens, which ensures that only air or water occupies a given cross-section of a lumen at a given time, as shown in FIG. 6C. Accordingly, the device 600 eliminates or greatly reduces cavitation to provide a silent liquid evacuation procedure.

Figure 7A:
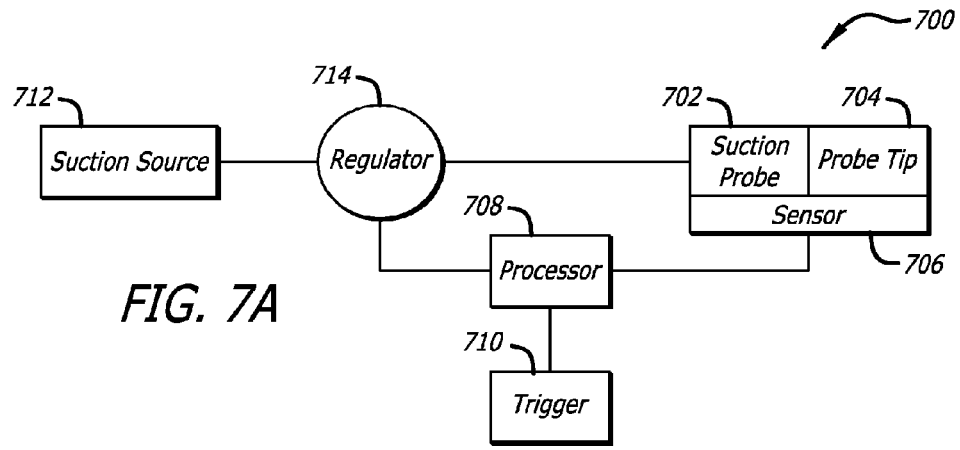
FIG. 7A shows a system diagram of a system for silently removing liquid from an ear, according to one embodiment of the invention.

Closed-Loop Control System:

FIG. 7A shows a system 700 for silently removing liquid from a patient's ear, according to one embodiment of the invention. The system 700 is configured to gate the rate of suction, to a device, using a closed loop control method. The system 700 includes a suction probe 702, which includes a probe tip 704, and at least one noise sensor 706. The suction probe 702 may be configured similarly to any of the devices disclosed herein, or may be a standard suction cannula. The sensor 706 may detect noise (e.g. sound) and/or pressure and/or flow rate at or about the probe tip 704, or any measureable artifact which is related to noise production. For example, as suction noise is caused by turbulence in a liquid stream, which is detectable at the fluid/air interface at the probe tip 704, detection of turbulence (e.g. presence, discontinuity, increase/decrease) may be used a detectable sensor artifact. Other measureable artifacts include heat/electrical conductivity (e.g. between two points in a probe using the liquid as a conductive medium where conductivity decreases with additional turbulence), evaporation, oxygen content, temperature, or some other micro-environmental variable. Alternatively, several sensors may monitor conditions throughout the entire suction probe 702. The sensor 706 is electronically coupled to a processor 708. The processor 708 may be a portion of an embedded computer. A trigger 710 sends user command signals to the processor 708, for example through a foot or hand switch. The suction probe 702 receives suction from a regulator 714 which is further connected to a suction source 712. The regulator 714 is electronically coupled to the processor 708. The processor 708 controls the regulator 714 to vary the rate and amount of negative pressure supplied to the suction probe 702. The sensor 706 may be configured to detect noise, or the imminent creation of a predetermined noise level, and indicate the noise detection to the processor. The processor 708 may modify, e.g. reduce or eliminate, negative pressure supplied to the suction probe 702 based on the sensor 706 signal. In one example, the sensor is used to sense a waveform which increases in amplitude. Thus, when the waveform increases to a predetermined level in velocity or amplitude, and/or accelerates at a predetermined rate, the processor 708 can reduce negative pressure to the suction probe 702. Accordingly, the imminent increase/creation of noise to a predetermined level can be abated, as the processor prevents the waveform from increasing. If no noise (e.g. no noise of a significant discomfort level) is sensed by the sensor 706, then the processor 708 may increase negative pressure to the suction probe until a predetermined level is reached. A test cycle may also be implemented by the processor on start-up or shut-down by sending a test pulse of negative suction to create a suction-wave in the system 700 to check if noise is initially present, which may occur if the probe tip is only partially submerged in liquid, before full negative pressure is enacted by the regulator. Thus, negative pressure may not be applied at a full rate and in a continuous mode if the probe is not fully immersed in liquid. Accordingly, the system 700 automatically prevents the creation of noise during a liquid evacuation procedure, and prevents discomfort to the patient.

The system 700 may include many of the components of a personal computer, such as a data bus, a memory, input and/or output devices (including a touch screen), and the like. The system 700 will often include both hardware and software, with the software typically comprising machine readable code or programming instructions for implementing one, some, or all of the methods described herein. The code may be embodied by a tangible media such as a memory, a magnetic recording media, an optical recording media, or the like. The system 700 may have (or be coupled to) a recording media reader, or the code may be transmitted to the processor 708 by a network connection such as an internet, an intranet, an Ethernet, a wireless network, or the like. Along with programming code, the system 700 may include stored data for implementing the methods described herein, and may generate and/or store data that records parameters reflecting the treatment of one or more patients.

Figure 7B:
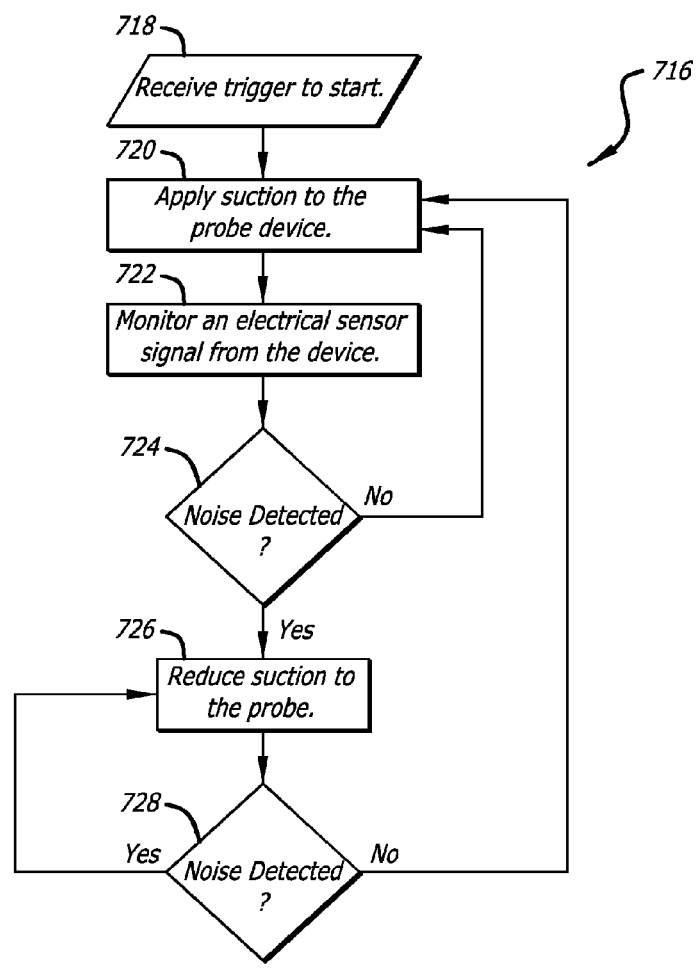
FIG. 7B shows a flow chart for a method for silently removing liquid from an ear, according to one embodiment of the invention.

FIG. 7B shows a method 716 for silently removing liquid from a patient's ear, which may be used with system 700, according to one embodiment of the invention. A trigger occurs at input 716 to supply suction to the suction probe 702. At operation 720 a processor 708 controls a regulator 714 to supply suction to a suction probe 702. At operation 722 a sensor 706 monitors noise at a probe tip 704 and sends a signal to the processor 708. At operation 724 it is determined whether the signal indicates noise, or imminent noise. If no noise, or imminent noise, is detected, then the method 716 loops back to operation 720. If noise, or imminent noise, is detected, then at operation 726 the processor 708 instructs the regulator 714 to reduce suction. At operation 728 it is again determined whether the signal indicates noise, or imminent noise, after suction reduction. If no noise, or imminent, noise is detected, then the method 716 loops back to operation 720. If noise, or imminent noise, is detected, then at operation 726 the processor 708 instructs the regulator 714 to reduce suction again. Accordingly, the method 716 automatically prevents the creation of noise during a liquid evacuation procedure, and prevents discomfort to the patient.

Figure 8A:
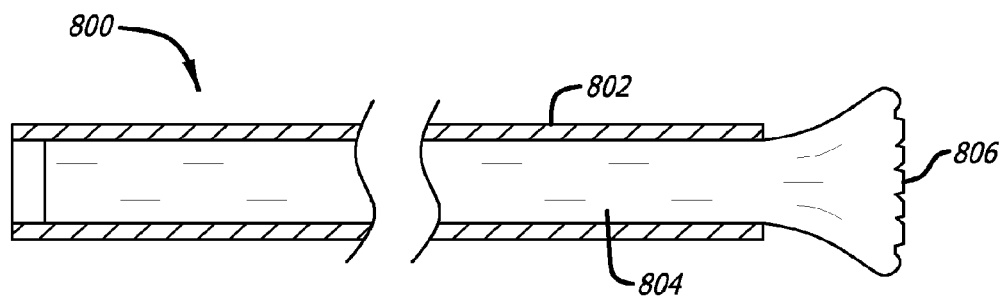
FIG. 8A shows a cross-sectional view of a device for silently removing liquid from an ear, according to one embodiment of the invention.
Figure 8B:
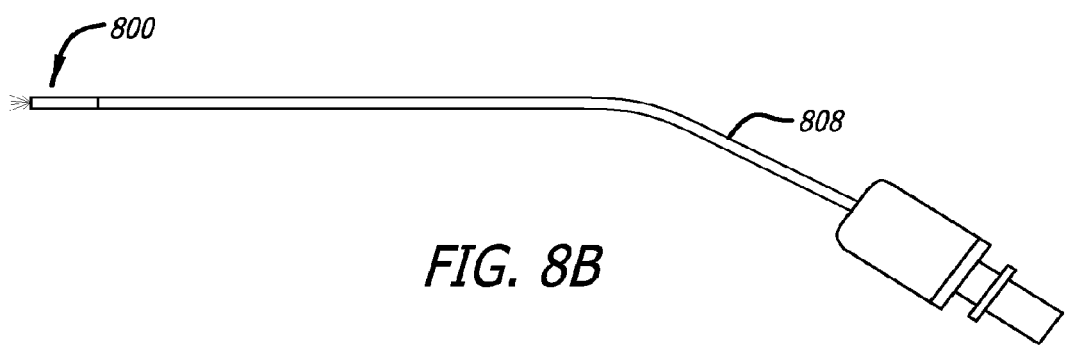
FIG. 8B shows a side view of the device of FIG. 8A coupled to a suction catheter, according to one embodiment of the invention.

FIG. 8A shows a device 800 for silently removing liquid from a patient's ear, according to one embodiment. The device 800 includes a cannula 802. In one embodiment the cannula 802 is a 0.075" ID/0.083" OD PTFE tube approximately 3.2 cm in length, with a 3/32" thick polyolefin material heat shrunk about the PTFE tube surface. The device 800 includes a filter material 804 within the cannula 802. In one embodiment the filter material is 65 thread count cotton gauze strands which are 1.5-1.7 cm long. In one embodiment, the filter material may be fibers of the cotton gauze longitudinally arranged within the cannula 802. Alternatively, the filter material may be constructed from porous foam strands. A portion 806 of the filter material 804 extends from the distal end of the cannula 802. The portion 806 may be frayed to resemble a mop head. The device 800 can be coupled to a commercially available 6 Fr suction catheter 808 as shown in FIG. 8B.

In use, the device 800 is applied to a liquid and/or light effusion within a patient's ear and suction is applied to the device 800, for example, by using the catheter 808. The filtering material 804 acts as a sound buffer by transferring the suction noise from the extreme distal end of the device to a more proximal location within cannula 802. In other words, the noise of suction does not occur at the extreme distal end, near the patient's ear drum, but instead occurs more proximally within cannula 802. Accordingly, the patient is protected from excessive noise due to the suction. The portion 806 extending from the cannula 802 may also cushion against unintended contact with portions of the ear canal and/or be used to physically abrade lodged effusion.

Figure 9A:
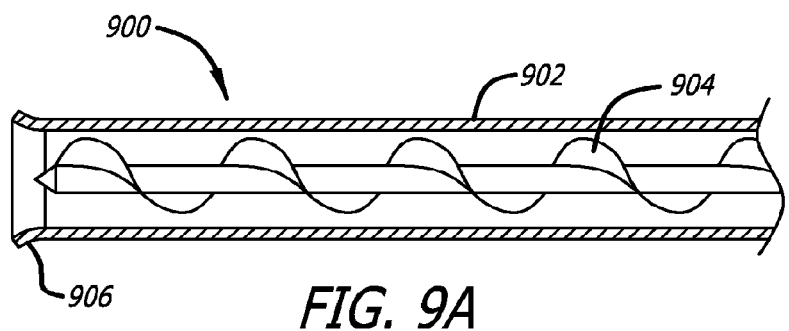
FIG. 9A shows a cross-sectional view of a device for removing liquid from an ear, according to one embodiment of the invention.
Figure 9B:
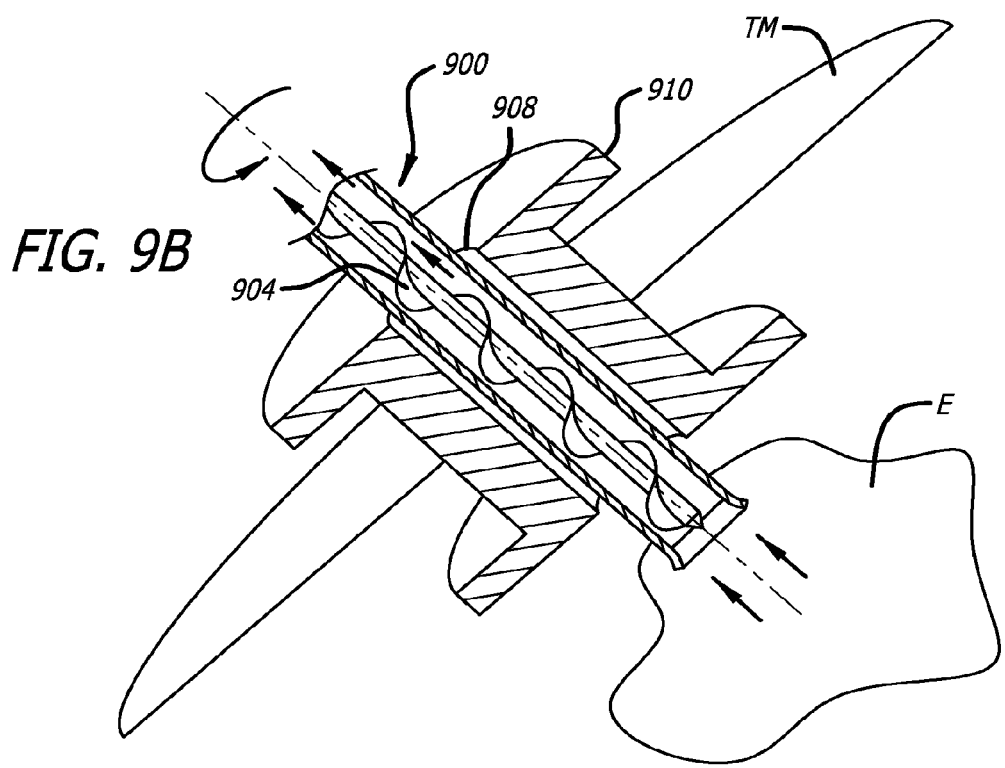
FIG. 9B shows a cross-sectional view of the device of FIG. 9A in use, according to one embodiment of the invention.

FIGS. 9A and 9B show a system for silently removing liquid from a patient's ear, according to one embodiment of the invention. The device 900 includes a cannula 902 and an Archimedes' screw 904 rotatably disposed within the cannula 902. The Archimedes' screw 904 may be coupled to a drive motor (not shown) to rotate at a relatively slow revolution, for example at 50-500 RPM, and at a constant torque. The cannula 902 may include a flared tip 906. The Archimedes' screw 904 may be configured to move in and out of the cannula. The cannula 902 may be configured to pass through a lumen 908 of a tympanostomy tube 910. A suction source may be coupled to the proximal end of the device 900.

In use, the tympanostomy tube 910 is first implanted within a tympanic membrane TM of an ear of a patient, as shown. Devices and methods for locally anesthetizing the tympanic membrane for such a tube implant procedure are disclosed in co-assigned patent applications U.S. Ser. No. 11/962,063 (now U.S. Pat. No. 8,192,420), U.S. Ser. No. 11/749,729 (published as U.S. Pub. No. 2008/0262510), now U.S. Pat. No. 9,387,124, issued Jul. 12, 2016), and U.S. 61/085,360, which were incorporated by reference above. The device 900 can then be inserted into the lumen 908 of the tympanostomy tube 910 and applied to a lodged effusion E. The Archimedes' screw 904 may rotate at a relatively slow RPM, and accordingly does not generate excessive noise, i.e. sputtering, to disturb the patient. Rotation of the Archimedes' screw 904 causes the effusion E to engage Archimedes' screw 904 and travel out of the ear canal. The Archimedes' screw 904 may rotate at a constant torque to prevent jamming with particularly thick effusion. The Archimedes' screw 904 may also be actuated in and out of the cannula to help disrupt the lodged effusion. Suction may be applied to the proximal portion of the device 900 to aid in effusion removal.

Figure 9C:
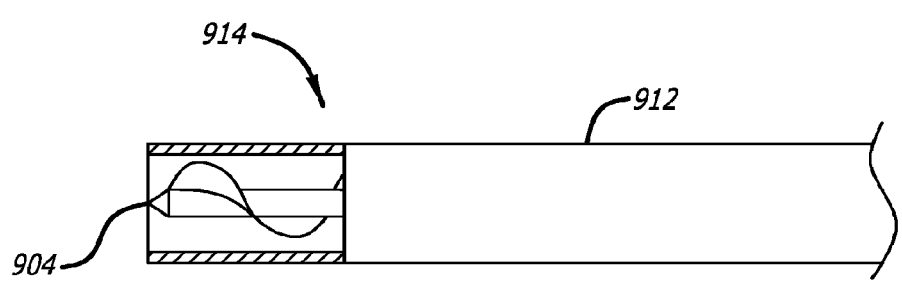
FIG. 9C shows a side view of an alternative embodiment of the device of FIG. 9A, according to one embodiment of the invention.

FIG. 9C shows an alternative embodiment of the device 900. A cannula 914 includes a laterally exposed portion 914, which exposes the tip of the Archimedes' screw 904. The exposed portion 914 may allow the Archimedes' screw 904 to help initiate transport of the effusion.

It should be noted that the silent liquid removal systems and devices shown and described herein may also be used to remove effusion. For example, the silent liquid systems and devices shown and described herein may be inserted into an ear canal to remove effusion. The silent liquid systems and devices shown and described herein may also be inserted directly into the middle ear, following a myringotomy or tympanostomy, to remove lodged effusion. Accordingly, the systems and devices for silent liquid removal described herein are not limited to removing liquid drug solution, and may be used to remove any liquid and fluidic particulates within the ear.

As will be understood by those skilled in the art, the present invention may be embodied in other specific forms without departing from the essential characteristics thereof. Those skilled in the art will recognize, or be able to ascertain using no more than routine experimentation, many equivalents to the specific embodiments of the invention described herein. Such equivalents are intended to be encompassed by the following claims.

What is claimed is:

1. A method for clearing effusion from a middle ear containing the effusion, the method comprising:
    (a) applying an ear device comprising a wicking tip to the effusion inside the middle ear, wherein the wicking tip has a proximal end and a distal end and comprises an absorbent material;
    (b) wicking the effusion from the middle ear, wherein the act of wicking the effusion comprises absorbing fluid from the middle ear via the distal end of the wicking tip; and
    (c) sealing and pressurizing the effusion inside the ear canal, the ear device regulating the amount of pressure inside the ear canal to aid in the act of wicking the effusion, wherein the wicking tip regulates turbulence to reduce noise caused by wicking the effusion.

2. The method of claim 1, wherein the wicking tip further comprises a porous material.

3. The method of claim 1, wherein negative pressure is applied to the device using a syringe, catheter or bulb.

4. The method of claim 1, wherein the device further comprises:
    (a) a syringe; and
    (b) a flexible nozzle, the flexible nozzle having:
        (i) a proximal end, and
        (ii) a distal end;
        wherein the proximal end of the flexible nozzle connects to the wicking tip of the device and the distal end of the flexible nozzle connects to the syringe.

5. The method of claim 4, wherein the flexible nozzle is constructed from polymers selected from the group consisting of: nylon, polycarbonate, polypropylene, polyethylene and silicone.

6. The method of claim 4, wherein the flexible nozzle is constructed from an alloy selected from the group consisting of: annealed alloy and super elastic alloy.

7. The method of claim 4, wherein the distal end of the flexible nozzle is coupled to the syringe with a luer lock.

8. A method for silently removing liquid from a patient's ear containing the liquid, the method comprising:
    (a) applying an ear device comprising a dry wicking tip to the liquid inside the ear to wick the liquid from the ear, wherein the wicking tip comprises an absorbent material;
    (b) wicking the liquid from inside the ear, wherein the act of wicking the liquid comprises absorbing the liquid from inside the ear via the absorbent material of the wicking tip; and
    (c) sealing and pressurizing the liquid inside the ear, the ear device regulating the amount of pressure inside the ear to aid in the act of wicking the liquid, wherein the wicking tip regulates turbulence caused by wicking the liquid from inside the ear.

9. The method of claim 8, wherein the act of wicking the liquid from inside the ear further comprises wicking liquid from inside an inner ear of the patient.

10. The method of claim 8, further comprising wicking liquid from inside a Eustachian tube of the patient.

11. The method of claim 8, wherein the wicking tip further comprises a porous material.

12. The method of claim 8, further comprising applying negative pressure to the device, wherein the act of applying negative pressure to the device comprises using a syringe, catheter or bulb.

13. The method of claim 8, wherein the device further comprises:
    (a) a syringe; and
    (b) a flexible nozzle, the flexible nozzle having:
        (i) a proximal end, and
        (ii) a distal end;
        wherein the proximal end of the flexible nozzle connects to the wicking tip of the device and the distal end of the flexible nozzle connects to the syringe.

14. The method of claim 13, wherein the flexible nozzle is constructed from polymers selected from the group consisting of: nylon, polycarbonate, polypropylene, polyethylene and silicone.

15. The method of claim 13, wherein the flexible nozzle is constructed from an alloy selected from the group consisting of: annealed alloy and super elastic alloy.

16. The method of claim 13, wherein the distal end of the flexible nozzle is coupled to the syringe with a luer lock.

17. A method for removing effusion from inside an ear canal of a patient, the method comprising:
    (a) applying an ear device comprising a wicking tip inside the ear canal to wick the effusion from the ear canal, wherein the wicking tip comprises an absorbent material;
    (b) wicking the effusion from inside the ear canal, wherein the act of wicking the effusion comprises absorbing the effusion from inside the ear canal via the absorbent material of the wicking tip; and
    (c) sealing and pressurizing the effusion inside the ear canal, the ear device regulating the amount of pressure inside the ear canal to aid in the act of wicking the effusion, wherein the wicking tip regulates turbulence caused by wicking the effusion from inside the ear canal.

18. The method of claim 17, further comprising a step of wicking liquid from inside a Eustachian tube of the patient.

19. The method of claim 17, further comprising applying negative pressure to the ear device, wherein the act of applying negative pressure to the ear device comprises using a syringe, catheter or bulb.

20. The method of claim 19, wherein the ear device further comprises:
    (a) a syringe; and
    (b) a flexible nozzle, the flexible nozzle having:
        (i) a proximal end, and
        (ii) a distal end;
        wherein the proximal end of the flexible nozzle connects to the wicking tip of the device and the distal end of the flexible nozzle connects to the syringe.

* * * * *